United States Patent [19]

Felix et al.

[11] Patent Number: 4,734,399
[45] Date of Patent: * Mar. 29, 1988

[54] GROWTH HORMONE RELEASING FACTOR ANALOGS

[75] Inventors: Arthur M. Felix, West Caldwell; Edgar P. Heimer, Sparta; Thomas F. Mowles, Pine Brook, all of N.J.

[73] Assignee: Hoffmann-La Roche Inc., Nutley, N.J.

[*] Notice: The portion of the term of this patent subsequent to Nov. 11, 2003 has been disclaimed.

[21] Appl. No.: 922,572

[22] Filed: Oct. 23, 1986

Related U.S. Application Data

[63] Continuation-in-part of Ser. No. 762,891, Aug. 6, 1985, Pat. No. 4,649,131, which is a continuation-in-part of Ser. No. 653,163, Sep. 24, 1984, Pat. No. 4,622,312.

[51] Int. Cl.$^4$ ................... A61K 37/43; C07K 7/10
[52] U.S. Cl. .................................. 514/12; 530/324
[58] Field of Search ......................... 514/12; 530/324

[56] References Cited

U.S. PATENT DOCUMENTS

| | | | |
|---|---|---|---|
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,605,513 | 8/1986 | DiMarchi | 530/303 |
| 4,605,643 | 8/1986 | Bohlen et al. | 514/12 |
| 4,610,976 | 9/1986 | Bohlen et al. | 530/324 |
| 4,617,149 | 10/1986 | DiMarchi et al. | 530/324 |
| 4,618,598 | 10/1986 | Conn | 530/313 |
| 4,622,312 | 11/1986 | Felix et al. | 530/324 |
| 4,649,039 | 3/1987 | Garlick et al. | 530/350 |
| 4,652,441 | 3/1987 | Okada et al. | 424/85 |

FOREIGN PATENT DOCUMENTS 2307584 1/1984 Australia .
0138416 2/1984 European Pat. Off. .

OTHER PUBLICATIONS

Guillemin et al., Science 218:585, (1982).

Hruby et al., eds., Peptides Structure and Function, pp. 853-856, (1983), Pierce Chemical Co., Rockford, Ill.
Lance et al., Biochem. Biophys. Res. Commun. 119:265, (1984).
Ling et al., Biochem., Biophys. Res. Commun. 123:854, (1984).
Rivier et al., Nature 300:276, (1982).

Primary Examiner—Delbert R. Phillips
Attorney, Agent, or Firm—Jon S. Saxe; George M. Gould; Norman C. Dulak

[57] ABSTRACT

The invention is directed to analogs of GRF or fragments thereof wherein the fragment is reduced in number by one to fifteen amino acids from the carboxyl end wherein the analogs have the formula:

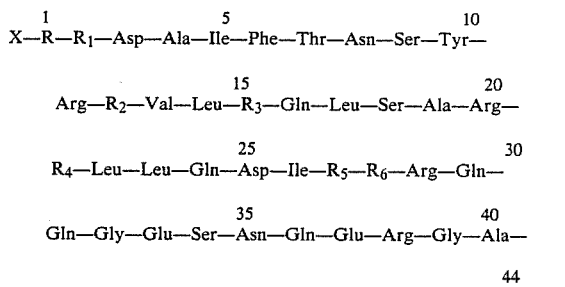

wherein R is desNH$_2$-Tyr, Tyr, D-Tyr, Ac-Tyr, His or C$^\alpha$-Methyl-Tyr; R$_1$ is Ala, N-Methyl-D-Ala or D-Ala; R$_2$ is Lys, Ala, Leu, Val or Ile; R$_3$ is Ala, Leu, Val, Ile, Nle, Nval, $\beta$-Ala or $\alpha$-Aib; R$_4$ is Lys, Ala, Leu, Val or Ile; R$_5$ is Met, Leu, Nle or Ile; R$_6$ is Asn or Ser; X is hydrogen or —COR$_7$; R$_7$ is hydrogen, C$_{1-4}$ alkyl or halo(C$_{1-4}$)alkyl; Y is —OR$_8$ or —NR$_9$R$_{10}$; R$_8$ is hydrogen or C$_{1-5}$-alkyl; R$_9$ and R$_{10}$ independently equal hydrogen, C$_{1-7}$ alkyl, C$_{2-4}$ alkenyl or halo(C$_{1-4}$)alkyl; and pharmaceutically acceptable acid or base addition salts thereof. The invention is further directed to pharmaceutical compositions and to methods for treating growth hormone deficiencies.

30 Claims, No Drawings

GROWTH HORMONE RELEASING FACTOR ANALOGS

This application is a continuation-in-part of copending U.S. application Ser. No. 762,891, filed Aug. 6, 1985, now U.S. Pat. No. 4,469,131, which in turn is a continuation-in-part of U.S. application Ser. No. 653,163, filed Sept. 24, 1984, now U.S. Pat. No. 4,622,312.

TECHNICAL FIELD

This invention relates to analogs of human growth hormone releasing factor and to fragments thereof, and to pharmaceutical compositions containing such analogs or fragments. The pharmaceutical compositions of the invention can be used to treat a variety of growth hormone related disorders in animals and in human beings.

BACKGROUND OF THE INVENTION

Growth hormone releasing factor (GRF) has been isolated from human islet cell tumor and structurally characterized by Guillemin et al. at the Salk Institute. Science 218: 585 (1982). The isolation and characterization of GRF eluded researchers for decades because the polypeptide was present in tissues in very small quantities. Human hypothalamic growth hormone releasing factor (hGRF) has been found to have the same structure as GRF isolated from islet cell tumor. Bohlen et al., Biochem. Biophys. Res. Commun. 114: 930 (1983).

Rivier et al., Nature 300: 276 (1982) have described the structure of GRF (1-44) and GRF (1-40) and have shown that GRF is specific for the release of growth hormone. These two forms of GRF are identical at the amino ($NH_2$-) terminus but differ in length. GRF (1-44) is further distinguished by the presence of an amide group at the carboxy terminus.

Rivier et al., supra, have shown that the biological activity of GRF resides in the $NH_2$-terminal portion of the molecule; full intrinsic activity and potency on a weight for weight basis was demonstrated with GRF(1-29)-$NH_2$ in vitro.

Lance et al., Biochem. Biophys. Res. Commun. 119: 265 (1984) have shown that GRF (1-29)-$NH_2$ having substitutions of selected amino acids at positions 1, 2 and 3 causes enhanced release of growth hormone (GH) in both pigs and rats in vivo. U.S. Pat. No. 4,518,586 discloses various GRF synthetic peptides, including one in which there is the substitution of D-Ala at position 15 for Gly. Similarly U.S. Pat. Nos. 4,528,190 and 4,529,595 disclose various GRF analogs, including the substitution of D-Ala at position 15 and Asn at position 28.

It is believed that growth in animals is regulated by a cascade of bioregulatory molecules. The hypothalamus produces GRF, which induces the release of growth hormone from the pituitary. Small quantities of GRF have been found to cause substantial pituitary release of growth hormone into the blood. Thus, GRF has great therapeutic utility in those instances where growth hormone administration is indicated. For example, GRF may be used in the treatment of hypopituitary dwarfism, diabetes due to growth hormone production abnormalities, promotion of wound and bone fracture healing, treatment of burns and retardation of the aging process. Similarly GRF has utility in the agricultural field. Examples of agricultural uses include enhanced meat production of fowl or animals raised for food such as pigs, cattle or the like to permit earlier marketing or to produce larger animals kept for similar time on feed, or improve the lean to fat ratios. GRF may also stimulate milk production in dairy cows and egg production in chickens.

SUMMARY OF THE INVENTION

The invention is directed to peptides of the formula:

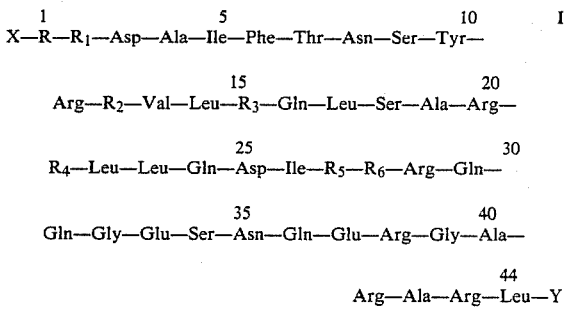

wherein R is Tyr, D-Tyr, desNH$_2$-Tyr, Ac-Tyr, His or C$^\alpha$-Methyl-Tyr; R$_1$ is Ala, N-Methyl-D-Ala or D-Ala; R$_2$ is Lys, Ala, Leu, Val or Ile; R$_3$ is Ala, Leu, Val, Ile, Nle, Nval, $\beta$-Ala or $\alpha$-Aib; R$_4$ is Lys, Ala, Leu, Val or Ile; R$_5$ is Met, Leu, Nle or Ile; R$_6$ is Asn or Ser; X is hydrogen or -COR$_7$; Y is -OR$_8$ or -NR$_9$R$_{10}$; R$_7$ is hydrogen, C$_{1-4}$ alkyl or halo(C$_{1-4}$)alkyl; R$_8$ is hydrogen or C$_{1-5}$ alkyl; R$_9$ and R$_{10}$ independently equal hydrogen, C$_{1-7}$alkyl, C$_{2-4}$alkenyl or halo(C$_{1-4}$)alkyl; or fragments thereof where the fragments are reduced in number by one to fifteen amino acids from the carboxyl end; and pharmaceutically acceptable acid or base addition salts thereof.

Pharmaceutical compositions in accordance with the invention include such analogs which are between twenty-nine (29) and forty-four (44) residues in length dispersed in a pharmaceutically acceptable liquid or solid carrier. Such pharmaceutical compositions can be used in clinical medicine, both human and veterinary, for administration in therapeutic and/or diagnostic applications. Moreover they can be used to promote the growth of warm and cold-blooded animals.

The peptides of this invention are useful in methods for stimulating the release of growth hormone from the pituitary for use in the treatments described above.

DETAILED DESCRIPTION OF THE INVENTION

The invention is directed to peptides having the formula:

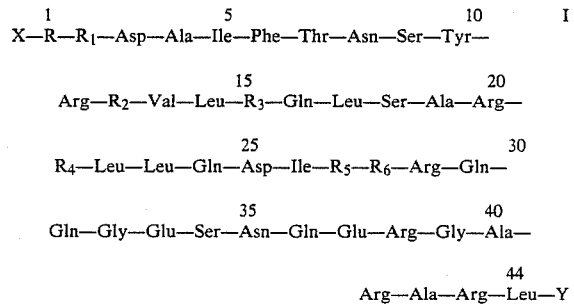

wherein R is Tyr, D-Tyr, desNH$_2$-Tyr, Ac-Tyr, His or C$^\alpha$-Methyl-Tyr; R$_1$ is Ala, N-Methyl-D-Ala or D-Ala; R$_2$ is Lys, Ala, Leu, Val or Ile; R$_3$ is Ala, Leu, Val, Ile, Nle, Nval, $\beta$-Ala or $\alpha$-Aib; R$_4$ is Lys, Ala, Leu, Val or Ile; R$_5$ is Met, Leu, Nle or Ile; R$_6$ is Asn or Ser; X is hydrogen or -COR$_7$; Y is -OR$_8$ or -NR$_9$R$_{10}$; R$_7$ is hydrogen, C$_{1-4}$ alkyl or halo(C$_{1-4}$)alkyl; R$_8$ is hydrogen or C$_{1-5}$ alkyl; R$_9$ and R$_{10}$ independently equal hydrogen, C$_{1-7}$alkyl, C$_{2-4}$alkenyl or halo(C$_{1-4}$)alkyl; or fragments thereof where the fragments are reduced in number by one to fifteen amino acids from the carboxyl end; and pharmaceutically acceptable acid or base addition salts thereof.

In a preferred embodiment, X is hydrogen, R is Tyr or desNH$_2$-Tyr, R$_1$ is Ala or D-Ala, R$_2$ is Lys or Ala, R$_3$ is Ala, R$_4$ is Lys or Ala, R$_5$ is Leu or Nle and R$_6$ is Asn or Ser, and the peptide comprises 32 amino acyl residues from the amino terminus and has a free acid carboxyl terminus.

The invention further relates to pharmaceutical compositions containing the novel peptides of formula I as the active agent in combination with a pharmaceutically acceptable or liquid or solid carrier as well as to the use of the novel peptides of the invention I in a method for promoting the growth of warm and cold-blooded animals as for example, humans, cattle, swine, fowl and fish. The peptides of formula I are especially useful in a method for treating growth hormone deficient humans, especially children as well as in a method for treating short-stature children.

The peptides of the invention are analogs of the naturally occuring human growth hormone releasing factor polypeptide. As used herein, the term "GRF" refers to the human growth hormone releasing factor which is a polypeptide having the amino acid sequence described in Science 218: 585 (1982).

Peptides of formula 1 which are between twenty-nine (29) and forty-four (44) amino acid residues are specifically contemplated within the scope of the present invention; especially preferred are the GRF analogs of formula I containing 29, 30, 32 or 40 residues and more preferably 29, 30 or 32 residues.

In accordance with conventional representation, the amino group at the N-terminus appears to the left and the carboxyl group at the C-terminus to the right. The term "amino acid" is used to mean one of the naturally occurring amino acids typically found in proteins, e.g., Gly, Ala, Val, Leu, Ile, Ser, Thr, Lys, Arg, Asp, Asn, Glu, Gln, Cys, Met, Phe, Tyr, Pro, Trp and His. Nle means norleucine, Nval means norvaline, $\alpha$-Aib refers to alpha-aminoisobutyric acid and $\beta$-Ala refers to beta-alanine. Where the amino acid residue has isomeric forms it is the L-form of the amino acid that is represented unless otherwise expressly indicated.

When the suffixes "-OH" and "-NH$_2$" are used following "GRF", they refer to the free acid and amide forms of the polypeptide, respectively. In the event neither suffix is used, the expression is intended to encompass both forms. Analogs of GRF are indicated by setting forth the substituted amino acid in parentheses before "GRF"; that is, for example, "(Ala$^{15}$)-GRF" indicates a polypeptide having an amino acid sequence corresponding to GRF in which an alanine residue has been substituted for glycine at position 15. Numbers in parentheses following "GRF" indicate fragments of the full polypeptide by giving the number of amino acid residues in the fragments. For example, GRF(1-29) indicates a fragment having the first 29 amino acids of the full sequence.

As used herein the term "C$_{1-4}$ alkyl" refers to straight chain or branched chain alkyl groups containing from one to four carbon atoms, e.g., methyl, ethyl, n-propyl, isopropyl, n-butyl, isobutyl, tert.-butyl and the like. The term "halo (C$_{1-4}$) alkyl" refers to alkyl groups containing from 1 to 4 carbon atoms which are substituted by chlorine, bromine, fluorine or iodine atoms, e.g., -CH$_2$Cl, -CHCl$_2$, -CH$_2$F, -CF$_3$, -CH$_2$CH$_2$Cl, -CH$_2$CCl$_3$ and the like. The term "C$_{2-4}$ alkenyl" refers to such groups as, e.g., -CH=CH$_2$, -CH$_2$CH=CH$_2$, -CH=CHCH$_2$, -CH$_2$CH$_2$CH=CH$_2$ and the like.

Representative peptides of the present invention are shown in Table 1.

TABLE 1

| X | R | R$_1$ | R$_2$ | R$_3$ | R$_4$ | R$_5$ | R$_6$ | Y |
|---|---|---|---|---|---|---|---|---|
| H | Tyr | Ala | Lys | Ala | Lys | Leu | Asn (Ser) | —NH$_2$ |
| —C(=O)CH$_3$ | D-Tyr | Ala | Leu | Ala | Ala | Met | Asn | —OH |
| —C(=O)C$_2$H$_5$ | D-Tyr | D-Ala | Ala | Leu | Leu | Leu | Asn | —OCH$_3$ |
| —C(=O)CH$_3$ | Tyr | N—Methyl-Ala | Leu | Val | Val | Met | Asn | —OC$_2$H$_5$ |
| H | D-Tyr | Ala | Val | Ala | Ileu | Ile | Asn | —OH |
| —C(=O)C$_3$H$_7$ | Tyr | N—Methyl-Ala | Lys | Ileu | Ala | Nle | Asn | —NHCH$_3$ |
| H | desNH$_2$Tyr | Ala | Ileu | Nle | Lys | Met | Asn | —NHC$_2$H$_5$ |
| —C(=O)CH$_3$ | Tyr | D-Ala | Val | Ile | Ala | Met | Asn | —N(CH$_3$)$_2$ |

TABLE 1-continued

| | | | Representative Peptides of Formula I | | | | | |
|---|---|---|---|---|---|---|---|---|
| X | R | R₁ | R₂ | R₃ | R₄ | R₅ | R₆ | Y |
| H | desNH₂—Tyr | Ala | Leu | Ala | Leu | Leu | Asn | —N(C₂H₅)₂ |
| H | His | Ala | Ala | Val | Ileu | Leu | Asn | —NHCH—CH₂ |
| H | Tyr | N—Methyl-Ala | Lys | Nle | Val | Met | Asn | —NHCH=CH₂ |
| O‖—CCH₃ | D-Tyr | Ala | Leu | NVal | Ala | Ile | Asn | —NH₂ |
| H | His | Ala | Val | Ala | Leu | Nle | Asn | —OH |
| H | Tyr | D-Ala | Ala | Ala | Leu | Met | Asn | —NHCCl₃ |

The polypeptides of this invention can be prepared by solid phase peptide synthesis techniques, solution phase peptide synthesis or by recombinant DNA methods. Recombinant DNA techniques may be used to prepare a portion of a peptide of the invention containing only naturally occurring amino acid residues, which may then be coupled to a short N-terminal peptide. Solid phase synthetic techniques such as that described by Merrifield, J. Am. Chem. Soc. 85: 2149 (1963) may be used to prepare the peptides of the invention, although other equivalent chemical synthetic methods known to one of ordinary skill may also be used.

Solid phase synthesis is commenced from the C-terminal end of the peptide by coupling a protected amino acid to a suitable resin. A starting material can be prepared by attaching an amino-protected amino acid via a benzyl ester linkage to a chloromethylated resin or a hydroxymethyl resin or via an amide bond to a benzhydrylamine (BHA) resin or methylbenzhydrylamine (MBHA) resin. These resins are available commercially and their preparation is known by one of ordinary skill in the art.

The acid form of the novel analogs may be prepared by the solid phase peptide synthesis procedure using a benzyl ester resin as a solid support. The polypeptide may be purified by preparative high performance liquid chromatography (HPLC) and then shown to be homogeneous by two analytical HPLC systems, isoelectric focusing and high voltage thin layer electrophoresis. Amino acid analysis may be performed so as to confirm the expected amino acid composition.

The corresponding amides may be produced by using benzhydrylamine or methylbenzhydrylamine resin as the solid support for solid phase peptide synthesis. Those skilled in the art will recognize that when the BHA or MBHA resin is used, treatment with anhydrous HF to remove the polypeptide from the solid support results in a polypeptide having a terminal amide group.

The C-terminal amino acid, Gly, is protected at the Nα-amino by t-butyloxycarbonyl (Boc). The Boc-Gly-OH can be first coupled to the resin using dicyclohexylcarbodiimide at about 25° C. for 2 hours with stirring. Following the coupling of the Boc protected amino acid to the resin support, the α-amino protecting group is removed, using trifluoroacetic acid (TFA) in methylene chloride or TFA alone. The deprotection is carried out at a temperature between about 0° C. and room temperature.

General methods for protecting and removing protecting groups from amino acids which can be used in this invention are described in The Peptides, Vol. 2 (E. Gross and J. Meienhofer, eds.) Academic Press, New York, pp. 1-284 (1979).

After removal of the α-amino protecting group, the remaining Boc-protected amino acids are coupled stepwise in the desired order or as an alternative to adding each amino acid separately in the synthesis, some may be coupled to one another prior to addition to the solid phase synthesizer. The selection of an appropriate coupling reagent is known to one of ordinary skill in the art. Particularly suitable is dicyclohexylcarbodiimide (DCC).

Each protected amino acid or peptide is introduced into the solid phase reactor is excess, and the coupling may be carried out in a medium of dimethylformamide (DMF) or methylene chloride (CH₂Cl₂) or mixtures thereof. In cases where incomplete coupling occurs, the coupling procedure is repeated before removal of the Nα-amino protecting group prior to the coupling of the next amino acid. The success of the coupling reaction at each stage of synthesis may be monitored. A preferred method of monitoring the synthesis is by the ninhydrin reaction. The coupling reactions can be performed automatically, as on a Vega 250 Peptide Synthesizer.

Cleavage of the peptide from the resin can be effected using procedures well known in peptide chemistry. Reaction with hydrogen fluoride in the presence of p-cresol and dimethylsulfide at 0° C. for 1 hour may be followed by a second reaction with hydrogen fluoride in the presence of p-cresol for 2 hours at 0° C.

Purification of the polypeptides of the invention can be effected using procedures well known in peptide chemistry. As previously indicated, the subject polypeptides may be purified using preparative HPLC; however, other known chromatographic procedures such as gel permeation, ion exchange and partition chromatography or countercurrent distribution can also be employed.

The polypeptides of this invention have growth hormone releasing activity. Pharmaceutical compositions in accordance with the invention include analogs of about 29 to 44 amino acids in length, or a nontoxic salt of any of these, dispersed in a pharmaceutically acceptable liquid or solid carrier. Such pharmaceutical compositions can be used for therapeutic or diagnostic purposes in clinical medicine, both human and veterinary. For example, they are useful in the treatment of growth-related disorders such as hypopituitary dwarfism and diabetes resulting from abnormalities in growth hormone production. Furthermore, they can also be used to stimulate the growth or enhance feed efficiency of animals raised for meat production, to enhance milk production and stimulate egg production.

Appropriate dosages of the polypeptides of the invention to be administered will vary somewhat depending on the individual subject and the condition being treated. The skilled worker will be able to determine appropriate dosages based on the known circulating levels of growth hormone associated with normal growth and the growth hormone releasing activity of the polypeptide. As is well known in the art, treatment of growth-related disorders will necessitate varying dosages from individual to individual depending upon the degree of insufficiency of growth hormone production.

Generally, a dosage range of from 0.04 μg/kg/day to about 1.0 μg/kg/day based on body weight of the subject may be used to stimulate release of growth hormone. The dosages employed to stimulate growth activity in livestock will be significantly higher (per kg. of subject weight) than the dosages employed to restore normal growth in cases of growth hormone deficiencies such as pituitary dwarfism in humans. In livestock generally a dosage in the range of from 0.4 μg/kg/day to about 10 μg/kg/day subcutaneously may be used to stimulate release of pituitary growth hormone.

The polypeptides of the invention can be administered in the form of human or veterinary pharmaceutical compositions which can be prepared by conventional pharmaceutical formulation techniques. Compositions suitable for oral, intravenous, subcutaneous, intramuscular, intraperitoneal or intranasal administration may be employed. A suitable dosage form for pharmaceutical use is from about 0.01 to about 0.5 mg of the compound of the invention, which may be lyophilized for reconstitution with sterile water or saline. The composition should be maintained at a pH below about 8.0 to maintain the stability of the analog. Serum albumin from the species being treated (e.g., human serum albumin in the case of humans, bovine serum albumin in the case of cows and so forth) may also be present together with other known pharmaceutical adjuvants.

The invention also relates to a method for treating growth-related disorders characterized by insufficient production of growth hormone which comprises administering an amount of the analogs of this invention sufficient to stimulate the production of growth hormone to levels associated with normal growth.

Normal levels of growth hormone vary considerably among individuals and, for any given individual, levels of circulating growth hormone vary considerably during the course of a day. In adult humans, normal serum levels of growth hormone have been reported to vary from about 0-10 nanograms/ml. In children, normal serum levels of growth hormone have been reported to vary from about 0-20 nanograms/ml.

To treat hypopituitary dwarfism effectively with the described analogs, treatment is administered during the period of normal growth. In females, this period generally does not extend far beyond the onset of menses. Thus, treatment of females should be withdrawn approximately from the age of 12 to 16 years, depending upon the individual. In males, the stimulation of growth may be possible for a considerably longer period of time beyond puberty. Thus, effective treatment of males will normally be possible up to about 18 to 19 years of age and, in some individual cases, up to about 25 years.

There is also provided a method of increasing the growth rate of animals by administering an amount of the analog sufficient to stimulate the production of growth hormone at a level greater than that associated with normal growth.

EXAMPLES

In the examples which follow, optically active protected amino acids in the L-configuration were employed except where specifically noted. The protected amino acids were examined by thin layer chromatography on silica gel G plates and developed with chlorine-TDM. Melting points were determined on a Thomas-Hoover apparatus (uncorrected) and optical rotation was measured in a jacketed 1 dm cell on a Perkin-Elmer Model 141 Polarimeter and conformed to the accepted values. Amino acid analysis was performed on a Waters Amino Acid Analyzer.

The following abbreviations are used in the examples to indicate various protecting groups and reagents.

| | |
|---|---|
| BOC = | t-butyloxycarbonyl |
| Z = | benzyloxycarbonyl |
| 2ClZ = | 2-chlorobenzyloxycarbonyl |
| Bzl = | benzyl |
| 2,6-Cl$_2$—Bzl = | 2,6-dichlorobenzyl |
| Tos = | p-toluenesulfonyl |
| DCC = | dicyclohexylcarbodiimide |
| BHA = | benzhydrylamine |
| PAM = | phenylacetamidomethyl |
| DMF = | dimethylformamide |
| TFA = | trifluoroacetic acid |
| CH$_2$Cl$_2$ = | methylene chloride |
| TGA = | thioglycolic acid |

The analogs of this invention were prepared by sequential coupling of amino acids using a commercially available automated solid phase peptide synthesizer (Vega 250 Peptide Synthesizer). Nα-Boc-amino acids were used in the synthesis.

Trifunctional amino acids were protected as Nα-Boc-Lys(2ClZ). Nα-Boc-Asp(OBzl), Nα-Boc-Glu(OBzl), Nα-Boc-Ser(Bzl), Nα-Boc-Thr(Bzl), Nα-Boc-Tyr(2,6-Cl$_2$-Bzl) and Nα-Boc-Arg(Tos).

The following examples are presented in order to illustrate the practice of this invention and are not to be construed as limiting the scope of the invention in any way. Unless otherwise stated, all parts and percents are given by weight and all temperatures are in degrees centigrade.

EXAMPLE 1

Preparation of [Ala$^{15}$,Leu$^{27}$,Asn$^{28}$]-GRF(1-32)-OH

Boc-Gly-PAM-resin (Vega Biochemicals, 8 g, 0.41 mM/g) was charged into the reaction vessel of a Vega 296 Peptide Synthesizer and solid phase peptide synthesis performed by the DCC procedure for a total of 5 cycles to give Boc-Leu$^{27}$-Asn$^{28}$-Arg(Tos)-GRF(32)-PAM-resin, (9.26 g). The PAM-resin, (0.7 g, 0.21 mmol) was charged into the reaction vessel of an Applied Biosystems 430A Peptide Synthesizer and solid phase synthesis performed by the symmetric anhydride procedure for a total of 26 cycles to give GRF [Ala$^{15}$,Leu$^{27}$,Asn$^{28}$] GRF-(1-32)-PAM-resin (1.3 g) which was treated with anhydrous HF (containing 10% DTE) for 2 h at 0°. The HF was evaporated at 0° (high-vac; CaO trap), and the crude peptide and resin mixture was triturated with EtOAc and extracted with TFA. The solvent was evaporated, and the residue was triturated with anhydrous ether and dried.

A portion (100 mg) of the crude material (0.524 g) was dissolved in 20 ml of 0.025% TFA/H$_2$O, centrifuged, filtered (0.45μ Type HA Millipore filter) and loaded onto a dual 1×25 cm Synchropak RP-P column system. The columns were then eluted with a linear gradient going from 25% CH$_3$CN (0.025% TFA)-H$_2$O to 40% CH$_3$CN (0.025% TFA)-H$_2$O in 120 minutes (with a flow rate of 2 ml/min). Fractions were collected (1 min/fraction) and aliquots analyzed by the analytical HPLC system. The product emerged in fractions 41 and 42 which were combined, evaporated and lyophilized to give pure [Ala$^{15}$,Leu$^{27}$,Asn$^{28}$]-GRF(1-32)-OH, yield: 3.2 mg.

The product was shown to be homogeneous by analytical HPLC and gave the expected amino acid composition (hydrolysis: 6N HCl containing 1% thioglycolic acid; 110° C.; 72 h): Asp, 4.10; Thr, 0.93; Ser, 2.13; Glu, 4.20; Gly, 1.00; Ala, 3.96; Val, 1.06; Ile, 1.89; Leu, 5.09; Tyr, 1.80; Phe, 0.94; Lys, 2.01; Arg, 2.88.

The biological activity of the claimed compounds were compared with that of synthetic GRF(1-44)-NH$_2$ which is comparable to the natural GRF(1-44)-NH$_2$. Biological activity of the synthetic GRF(1-44)-NH$_2$ was identical to the natural GRF(1-44)-NH$_2$ which was isolated from a human pancreatic tumor of an individual suffering from acromegaly (Salk Institute standard hGRF-NH$_2$(NL-A-10)). The assay for biological activity, which is based on the ability to stimulate production of growth hormone in rat pituitary cells in tissue culture, was performed as discribed in Example 2.

EXAMPLE 2

Biological Activity of [Ala$^{15}$, Leu$^{27}$, Asn$^{28}$]-GRF(1-32)-OH and Other GRF Analogs Pituitaries from 30-40 male Sprague-Dawley rats (175 g) were removed aseptically after decapitation. The anterior lobes were collected, washed 3 times in sterile Hepes buffer (0.025M) (pH 7.35) and dispersed at 37° C. in 20-30 ml Hepes buffer (pH 7.35) containing collagenase (4 mg per ml) and Dispase (Protease grade II, 2 mg per ml). After gentle 100-110 min vortexing and trituration by Pasteur pipette, the dispersed cells were separated by centrifugation (150×g, 4 min) and re-suspended in Hepes buffer containing neuraminidase (8 g/ml), and 200 g/ml ethylenediaminetetraacetic acid (EDTA) disodium salt, pH 7.35, for 10 min.

The cells were washed twice with plating medium and plated on multiwell-plates (1.5×10$^5$ cells per ml) using the following defined medium: F-12/DMEM/BGJ (6:3:1) (Gibco: 430-1700/430-1600/320-2591) with 2 g BSA/l., 2.38 g Hepes/1.50 mg PSN antibiotic mixture (Gibco Laboratories), 10 mg/l transferrin (Sigma T2252) with 1.83 g NaHCO$_3$/l (Baker 3506). The medium in each well was supplemented either with a sample of the novel GRF peptide or natural GRF(1-44)-NH$_2$ at concentrations ranging from 0.8 to 200 fmol per ml of medium. Control wells contained no supplement. Plating was done with this medium added with 2% fetal calf serum to ensure rapid fixation of the cells.

On the fourth day, the cells were washed twice with the defined medium without fetal calf serum. Finally 900 μl of defined medium was added to each well plus 100 μl of the same medium containing each individual treatment, in triplicate. After 4 hours of incubation the medium was collected and diluted as required to conduct radioimmunoassay (RIAs) for rat growth hormone.

RIAs for rat growth hormone were conducted using Sinha's anti-murine GH immune serum and procedures according to the National Pituitary Agency using protein A to precipitate antibody antigen complex. The results are summarized in Table 2.

TABLE 2

| Peptide of [Ala$^{15}$,Leu$^{27}$,Asn$^{28}$]—GRF(1-32)-OH Potency Relative to GRF(1-44)-NH$_2$ | |
|---|---|
| Exp. #GB 83 | |
| GRF(1-29)NH$_2$ | 0.5 |
| GRF(1-44)NH$_2$ | 1.0 |
| [Ala$^{15}$,Leu$^{27}$,Asn$^{28}$]—GRF(1-32)-OH | 2.2 |

The peptides of the invention are useful for human applications in which a physician wishes to elevate GH production. Stimulation of GH secretion by the peptides of the invention is of interest in patients with complete or relative GH deficiency caused by underproduction of endogenous GRF. Furthermore, it is probable that increased GH secretion and its attendant increase in growth could be obtained in humans or animals with normal GH levels. Moreover, administration should alter body fat content and modify other GH-dependent metabolic, immunologic and developmental processes.

For example, the peptides of the invention may be useful as a means of stimulating anabolic processes in human beings for the treatment of burns, etc. As another example, the peptides of the invention may be administered to commercial warm-blooded animals, such as chickens, turkeys, pigs, goats, cattle and sheep, and may be used in aquiculture for raising fish and other cold-blooded marine animals, e.g., sea turtles and eels, and amphibians, to accelerate growth and increase the ratio of protein to fat gained by administering effective amounts of the peptides.

For administration to humans, the peptides of the invention should have a purity of at least about 93% and preferably at least 98%. As used herein the term "purity" refers to the intended peptide constituting the stated weight% of all peptides and peptide fragments present. For the administration of such synthetic peptides to commercial and other animals in order to promote growth and reduce fat content, a purity as low as about 3%, or even as low as 0.01%, may be acceptable.

The peptides of the invention or the nontoxic salts thereof, combined with a pharmaceutically acceptable carrier to form a pharmaceutical composition, may be administered to animals, including humans, either intravenously, subcutaneously, intramuscularly, intranasally or orally. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of nontoxic salts such as acid addition salts or metal complexes, e.g., with zinc, iron, or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like.

If the active ingredient is to be orally administered in tablet form, the tablet may contain a binder such as tragacanth, corn, starch, or gelatin, a distintegrating agent, such as alginic acid and a lubricant such as magnesium stearate. If administration in liquid form is desired, sweetening and/or flavoring may be used, and intravenous administration with isotonic saline used as the liquid carrier or phosphate buffer solutions or the like may be effected.

Many modifications and variations of this invention may be made without departing from its spirit and scope, as will become apparent to those skilled in the art. The specific embodiments described herein are offered by way of example only, and the invention is limited only by the terms of the appended claims.

What is claimed is:

1. A peptide of the formula

```
 1                      5                    10
X—R—R₁—Asp—Ala—Ile—Phe—Thr—Asn—Ser—Tyr—

15                      20
Arg—R₂—Val—Leu—R₃—Gln—Leu—Ser—Ala—Arg—

25                      30
R₄—Leu—Leu—Gln—Asp—Ile—R₅—R₆—Arg—Gln—

35                      40
Gln—Gly—Glu—Ser—Asn—Gln—Glu—Arg—Gly—Ala—

44
                    Arg—Ala—Arg—Leu—Y
``` wherein R is desNH₂-Tyr, Tyr, D-Tyr, Ac-Tyr, His or C$^\alpha$-Methyl-Tyr; R₁ is Ala, N-Methyl-D-Ala or D-Ala; R₂ is Lys, Ala, Leu, Val or Ile; R₃ is Ala, Leu, Val, Ile, Nle, Nval, β-Ala or α-Aib; R₄ is Lys, Ala, Leu, Val or Ile; R₅ is Met, Leu, Nle or Ile; R₆ is Asn or Ser; X is hydrogen or -COR₇; R₇ is hydrogen, C₁₋₄ alkyl or halo(C₁₋₄)alkyl; Y is -OR₈ or -NR₉R₁₀; R₈ is hydrogen or C₁₋₅-alkyl; R₉ and R₁₀ independently equal hydrogen, C₁₋₇ alkyl, C₂₋₄-alkenyl or halo(C₁₋₄)alkyl; or a fragment thereof where the fragment is reduced in number by one to fifteen amino acids from the carboxyl end; or a pharmaceutically acceptable acid or base addition salt thereof.

2. The peptide of claim 1 in which R₆ is Asn.

3. The peptide of claim 2 in which R is des NH₂-Tyr or Tyr.

4. The peptide of claim 3 in which R₁ is Ala, N-Methyl-D-Ala or D-Ala.

5. The peptide of claim 4 in which R₃ is Ala.

6. The peptide of claim 2 which comprises 29, 30, 32 or 40 amino acids, starting from the amino terminus.

7. The peptide of claim 5 in which R₄ is Ala or Lys and X is hydrogen.

8. The peptide of claim 5 in which R₂ is Ala or Lys and X is hydrogen.

9. The peptide of claim 2 in which R₅ is Leu.

10. The peptide of claim 1 in which X is hydrogen, R is Tyr or desNH₂-Tyr, R₁ is Ala or D-Ala, R₂ is Lys or Ala, R₃ is Ala, R₄ is Lys or Ala, R₅ is Leu or Nle and R₆ is Asn or Ser, which peptide comprises 32 amino acyl residues from the amino terminus and has a free acid carboxyl terminus.

11. A pharmaceutical composition comprising as the active agent a peptide or a pharmaceutically acceptable acid or base addition salt thereof wherein said peptide has the formula

```
 1                      5                    10
X—R—R₁—Asp—Ala—Ile—Phe—Thr—Asn—Ser—Tyr—

15                      20
Arg—R₂—Val—Leu—R₃—Gln—Leu—Ser—Ala—Arg—

25                      30
R₄—Leu—Leu—Gln—Asp—Ile—R₅—R₆—Arg—Gln—

35                      40
Gln—Gly—Glu—Ser—Asn—Gln—Glu—Arg—Gly—Ala—

44
                    Arg—Ala—Arg—Leu—Y
``` wherein R is desNH₂-Tyr, Tyr, D-Tyr, Ac-Tyr, His or C$^\alpha$-Methyl-Tyr; R₁ is Ala, N-Methyl-D-Ala or D-Ala; R₂ is Lys, Ala, Leu, Val or Ile; R₃ is Ala, Leu, Val, Ile, Nle, Nval, β-Ala or α-Aib; R₄ is Lys, Ala, Leu, Val or Ile; R₅ is Met, Leu, Nle or Ile; R₆ is Asn or Ser; X is hydrogen or -COR₇; R₇ is hydrogen, C₁₋₄ alkyl or halo(C₁₋₄)alkyl; Y is -OR₈ or NR₉R₁₀; R₈ is hydrogen or C₁₋₅-alkyl; R₉ and R₁₀ independently equal hydrogen, C₁₋₇ alkyl, C₂₋₄-alkenyl or halo(C₁₋₄)alkyl; or a fragment thereof where the fragment is reduced in number by one to fifteen amino acids from the carboxyl end; or a pharmaceutically acceptable acid or base addition salt thereof; and a pharmaceutically acceptable solid or liquid carrier.

12. The pharmaceutical composition of claim 11 in which R₆ is Asn.

13. The pharmaceutical composition of claim 12 in which R is desNH₂-Tyr or Tyr.

14. The pharmaceutical composition of claim 13 in which R₁ is Ala, N-Methyl-D-Ala or D-Ala.

15. The pharmaceutical composition of claim 14 in which R₃ is Ala.

16. The pharmaceutical composition of claim 12 in which the peptide comprises 29, 30, 32 or 40 amino acids, starting from the amino terminus.

17. The pharmaceutical composition of claim 15 in which R₄ is Ala or Lys and X is hydrogen.

18. The pharmaceutical composition of claim 15 in which R₂ is Ala or Lys and X is hydrogen.

19. The pharmaceutical composition of claim 12 in which R₅ is Leu.

20. The pharmaceutical composition of claim 11 in which X is hydrogen, R is Tyr or desNH₂-Tyr, R₁ is Ala or D-Ala, R₂ is Lys or Ala, R₃ is Ala, R₄ is Lys or Ala, R₅ is Leu or Nle and R₆ is Asn or Ser, which peptide comprises 32 amino acyl residues from the amino terminus and has a free acid carboxyl terminus.

21. A method for treating growth related disorders characterized by growth hormone deficiencies comprising administering to an animal in need of such treatment an effective amount of a peptide of the formula

```
 1                      5                    10
X—R—R₁—Asp—Ala—Ile—Phe—Thr—Asn—Ser—Tyr—

15                      20
Arg—R₂—Val—Leu—R₃—Gln—Leu—Ser—Ala—Arg—

25                      30
R₄—Leu—Leu—Gln—Asp—Ile—R₅—R₆—Arg—Gln—

35                      40
Gln—Gly—Glu—Ser—Asn—Gln—Glu—Arg—Gly—Ala—

44
                    Arg—Ala—Arg—Leu—Y
``` wherein R is desNH₂-Tyr, Tyr, D-Tyr, Ac-Tyr, His or C$^\alpha$-Methyl-Tyr; R₁ is Ala, N-Methyl-D-Ala or D-Ala; R₂ is Lys, Ala, Leu, Val or Ile; R₃ is Ala, Leu, Val, Ile, Nle, Nval, β-Ala or α-Aib; R₄ is Lys, Ala, Leu, Val or Ile; R₅ is Met, Leu, Nle or Ile; R₆ is Asn or Ser; X is hydrogen or -COR₇; R₇ is hydrogen, C₁₋₄ alkyl or halo($C_{1-4}$)alkyl; Y is -$OR_8$ or -$NR_9R_{10}$; $R_8$ is hydrogen or $C_{1-5}$-alkyl; $R_9$ and $R_{10}$ independently equal hydrogen, $C_{1-7}$ alkyl, $C_{2-4}$-alkenyl or halo($C_{1-4}$)alkyl; or a fragment thereof where the fragment is reduced in number by one to fifteen amino acids from the carboxyl end; or a pharmaceutically acceptable acid or base addition salt thereof; and a pharmaceutically acceptable solid or liquid carrier.

22. The method of claim 21 in which $R_6$ is Asn.

23. The method of claim 22 in which R is desNH$_2$-Tyr or Tyr.

24. The method of claim 23 in which $R_1$ is Ala, N-Methyl-D-Ala or D-Ala.

25. The method of claim 24 in which $R_3$ is Ala.

26. The method of claim 22 in which the peptide comprises 29, 30, 32 or 40 amino acids from the amino terminus.

27. The method of claim 25 in which $R_4$ is Ala or Lys and X is hydrogen.

28. The method of claim 25 in which $R_2$ is Ala or Lys and X is hydrogen.

29. The method of claim 22 in which $R_5$ is Leu.

30. The method of claim 21 in which X is hydrogen, R is Tyr or desNH$_2$-Tyr, $R_1$ is Ala or D-Ala, $R_2$ is Lys or Ala, $R_3$ is Ala, $R_4$ is Lys or Ala, $R_5$ is Leu or Nle and $R_6$ is Asn or Ser, which peptide comprises 32 amino acyl residues from the amino terminus and has a free acid carboxyl terminus.

* * * * *